United States Patent [19]

Wade

[11] 4,160,449

[45] Jul. 10, 1979

[54] EARPLUG

[76] Inventor: Kenneth L. Wade, Box 22, Croton-on-Hudson, N.Y. 10520

[21] Appl. No.: 837,530

[22] Filed: Sep. 28, 1977

[51] Int. Cl.² .............................................. A61F 11/02
[52] U.S. Cl. ................................................... 128/152
[58] Field of Search ............................... 128/152, 151

[56] References Cited

U.S. PATENT DOCUMENTS

| | | | |
|---|---|---|---|
| 2,672,863 | 3/1954 | Leight | 128/152 |
| 3,771,521 | 11/1973 | Kittredge | 128/152 |
| 3,872,559 | 3/1975 | Leight | 128/152 |

*Primary Examiner*—Henry J. Recla
*Attorney, Agent, or Firm*—Robert E. Burns; Emmanuel J. Lobato; Bruce L. Adams

[57] ABSTRACT

An earplug comprises a generally cylindrical plug of compressible resilient elastomeric foam having a diameter in relaxed condition slightly larger than the outer canal of a human ear and an envelope of thin plastic material which encases the plug and has a portion extending lengthwise beyond the end of the plug. The envelope is twistable to compress and thereby reduce the size of the plug to facilitate insertion of the plug into the outer ear canal. The envelope also provides a convenient means of extracting the plug. The envelope may be open to the atmosphere—while retaining the plug—so that air can be squeezed out of the plug and envelope or it may be sealed and evacuated so as to provide lower than atmospheric pressure inside the envelope.

9 Claims, 6 Drawing Figures

EARPLUG

FIELD OF INVENTION

The present invention relates to plugs that are insertable in the outer canal of the ear to protect the ear from noise for example in a noisy environment or protection from water when swimming.

BACKGROUND OF THE INVENTION

Various types of earplugs have heretofore been proposed. Thus Wade U.S. Pat. No. 2,262,568 discloses an ear protector comprising a porous latex body of generally cylindrical form one section of which is impregnated with a waxy material. Kittredge U.S. Pat. No. 3,771,521 discloses an earplug comprising an elongated slug of nonslumping silicone putty enclosed in a thin cocoon of synthetic organic polmeric film drawn over the tip end of the earplug and gathered at the base by a tie off member. Gardner U.S. Pat. No. 3,811,437 discloses a generally cylindrical earplug composed of a resilient plasticized polymeric foam having a sufficiently high concentration of organic plasticizer therein as to provide a slow rate of recovery. While these earplugs have, at least to some extent, fulfilled the intended purpose they have left considerable room for improvement.

SUMMARY OF THE INVENTION

It is an object of the present invention to provide an improved earplug which can be easily inserted in the outer canal of the ear, is highly effective in use and can easily be withdrawn. Moreover, the earplugs in accordance with the present invention can be easily and economically manufactured.

In accordance with the invention there is provided an earplug comprising a generally cylindrical plug of soft, resilient spongy material, for example elastomeric foam, having a diameter in relaxed condition slightly larger than the outer canal of a human ear. The soft resilient plug is encased in an envelope of thin flexible plastic material which extends lengthwise beyond the end of the plug. The envelope is twistable to compress the plug and thereby reduce its size so as to facilitate introduction of the plug into the outer ear canal.

While the envelope is closed sufficiently to retain the plug therein, it may be open to the atmosphere so that air can be expelled from the plug and the interior of the envelope when the latter is compressed and twisted. Alternatively, the envelope is sealed and the space therein evacuated so as to provide a lower than atmospheric pressure inside the envelope. The sound attenuating characteristics of the plug are thereby increased.

BRIEF DESCRIPTION OF DRAWINGS

The nature, objects and advantages of the invention will be more fully understood from the following description of preferred embodiments illustrated by way of example in the following drawings in which.

DESCRIPTION OF PREFERRED EMBODIMENTS

Figure 1:
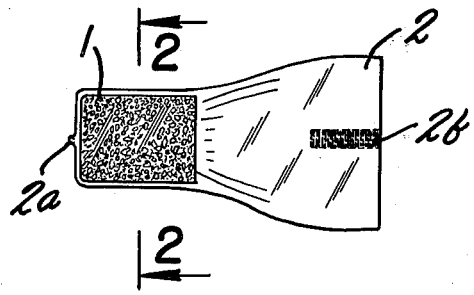
FIG. 1 is a side view of an earplug in accordance with the present invention.
Figure 2:
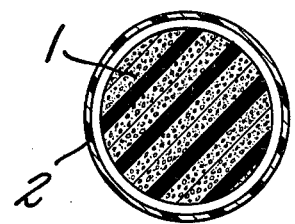
FIG. 2 is a schematic enlarged cross section taken approximately on the line 2—2 in FIG. 1.

As illustrated by way of example in the drawings, an earplug in accordance with the present invention comprises a generally cylindrical plug 1 of compressible, resilient elastomeric foam in a bag or envelope 2 of thin plastic material.

The material of which the plug is formed is a medium density foam of elastomeric material such as polyurethane foam, foam rubber or silicone rubber foam having the characteristics of being soft so that it can be easily compressed and elastic and resilient so that it resumes its original size and shape when released. The foam may be of open cell or closed cell type but for most purposes closed cell foam is preferred. The plugs can conveniently be die cut from foam sheet material having a thickness equal to the desired length of the plugs or can be cut from foam material in the form of a rod having the desired diameter.

The bag or envelope 2 is formed of thin highly flexible plastic sheet material which preferably has a thickness of about 0.001 to 0.0015". By way of example the envelope may be of polyethelene, polyvinylchloride or saran (polyvinylidene chloride) such as that sold by the Dow Chemical Company under the trade name of Saran Wrap. The envelope is generally tubular and is of a diameter to receive the plug fairly snugly but not tightly. For example the diameter of the envelope may be about 0.1" greater than the diameter of the plug. The envelopes are conveniently formed by welding or adhesively securing the edges of a strip of the plastic sheet material together to form a tube and the cutting off lengths of the tube. Alternatively, a tube can be formed by extrusion and then cut into suitable lengths. The length of the envelope is greater than that of the plug so that the envelope extends lengthwise beyond the end of the plug. For example the length of the envelope may be two or three times the length of the plug.

The inner end of the envelope 2 is closed for example by welding as indicated at 2a. In the embodiment illustrated in FIG. 1 (where the right hand portion of the envelope 2 is shown flattened) the outer end of the envelope is partially closed, for example by a welded area 2b, so as to retain the plug in the envelope. However, the envelope is otherwise open to the atmosphere so that air can be expelled from the interior of the envelope. In some instances, for example to permit equalization of pressure or to permit ventilation of culture materials within a bottle when the plug is used for a bottle closure, the envelope may be provided with a multiplicity of small performations permitting the passage of air.

Figure 3:
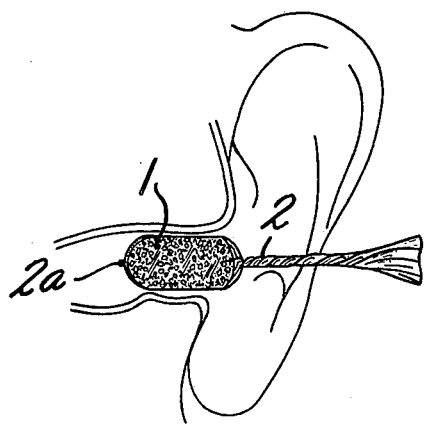
FIG. 3 is a schematic view showing how the envelope is twisted to compress the plug for insertion in the outer ear canal.
Figure 4:
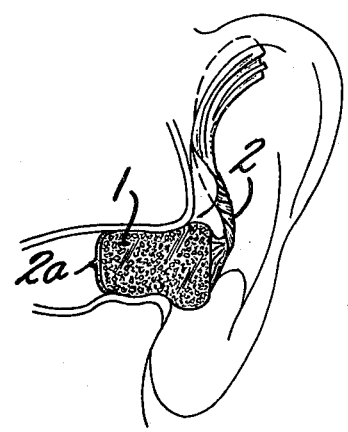
FIG. 4 is a schematic view showing how the earplug has expanded in the outer ear canal.

An earplug in accordance with the present invention is used as illustrated schematically in FIGS. 3 and 4. By compressing the plug with the fingers and twisting the envelope so as to reduce the size of the plug, the plug can easily be inserted in the outer canal of the ear as illustrated in FIG. 3. The plug is then released so that it expands in the ear canal as illustrated in FIG. 4. In expanded condition the plug conforms to the ear canal by reason of its resilience and the envelope assists in making good contact between the plug and the surface of the ear canal. Effective attenuation of sound is thereby assured. The tail end of the envelope can, if desired, be tucked up inside the outer ear as illustrated schematically in FIG. 4. When it is desired to withdraw the plug, the envelope provides a convenient means for effecting the withdrawal. The compression of the plug for insertion assures better placement of the plug within the ear opening so as to make an effective seal when the plug expands.

Figure 5:
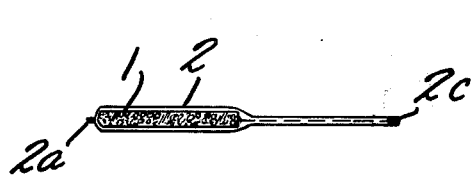
FIG. 5 is a side view illustrating a modified construction in which the plug and envelope are flattened and the envelope is sealed in this condition.
Figure 6:
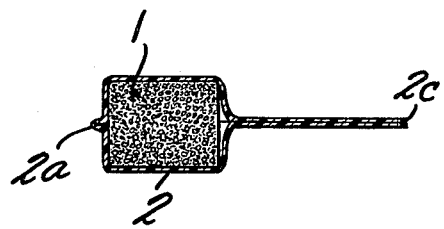
FIG. 6 is a schematic cross sectional view illustrating how the plug of FIG. 5 has expanded so as to create a reduced pressure inside the envelope.

FIGS. 5 and 6 illustrate a modification in accordance with which the plug and envelope are flattened as illustrated in FIG. 5 so as to expel most of the air from the plug and from the interior of the envelope. The envelope is then hermetically sealed as indicated at 2c while in flattened condition. When the plug is released it expands as illustrated in FIG. 6 with the result that a subatmospheric pressure prevails in the interior of the envelope. If the envelope is made of a highly impervious film such as saran, the reduced pressure inside the envelope is maintained for a long period of time. By reason of the reduced pressure in the envelope, the transmission of sound through the plug is reduced whereby the plug becomes more effective for sound attenuation. The earplug shown in FIGS. 5 and 6 is used in the same manner as described above and illustrated in FIGS. 3 and 4.

While preferred embodiments of the invention have been illustrated in the drawings and are herein particularly described, it will be understood that variations and modifications may be made and that the invention is hence in no way limited to the illustrated embodiments.

What I claim is:

1. An earplug comprising a generally cylindrical plug of soft compressible resilient spongy material, said plug having a diameter in relaxed condition slightly greater than the average diameter of the outer canal of a human ear, and a tubular envelope of thin flexible plastic material which is closed at its inner end and receives said plug snugly but not tightly, said envelope having an outer end portion that extends beyond the outer end of said plug, means at least partially closing said extending portion of said envelope at a distance from the outer end of said plug to retain said plug in said envelope, said extending portion of said envelope being twistable to compress said plug and thereby reduce its diameter to facilitate introduction of said plug into the outer ear canal, whereupon said envelope is released to permit said plug to expand to conform to the outer ear canal.

2. An earplug according to claim 1, in which said envelope has a thickness of about 1 mil.

3. An earplug according to claim 1, in which said envelope has a length between two and three times the length of said plug.

4. An earplug according to claim 1, in which said envelope is closed sufficiently to retain said plug therein but is open to the atmosphere, whereby air can be expelled therefrom by said twisting.

5. An earplug according to claim 1, in which said envelope is sealed and the space therein is evacuated to lower than atmospheric pressure inside the envelope.

6. An earplug according to claim 1, in which said plug is of elastomeric foam.

7. An earplug according to claim 6, in which said elastomeric foam is of closed cell type.

8. An earplug according to claim 1, in which the diameter of said tubular envelope is about 0.1 inch greater than the diameter of said plug.

9. An earplug comprising a generally cylindrical plug of soft compressible resilient spongy material, said plug having a diameter in relaxed condition slightly greater than the average diameter of the outer canal of a human ear, and a tubular envelope of thin flexible impervious plastic material which is closed at its inner end and encases said plug, an outer end portion of said envelope extending beyond said plug, both ends of said envelope being hermetically sealed and the space in said envelope being at lower than atmospheric pressure, said outer end portion of said envelope being twistable to compress said plug and thereby reduce its diameter to facilitate introduction of said plug into the outer ear canal, whereupon said envelope is released to permit said plug to expand to conform to the outer ear canal.

* * * * *